US012035982B2

(12) United States Patent
O'Connor

(10) Patent No.: US 12,035,982 B2
(45) Date of Patent: Jul. 16, 2024

(54) SYSTEMS AND METHODS FOR SURGICAL NAVIGATION

(71) Applicant: NuVasive, Inc., San Diego, CA (US)

(72) Inventor: Sean O'Connor, San Diego, CA (US)

(73) Assignee: Globus Medical, Inc, Audubon, PA (US)

( * ) Notice: Subject to any disclaimer, the term of this patent is extended or adjusted under 35 U.S.C. 154(b) by 552 days.

(21) Appl. No.: 17/373,297

(22) Filed: Jul. 12, 2021

(65) Prior Publication Data
US 2023/0008222 A1    Jan. 12, 2023

(51) Int. Cl.
*G06K 9/00* (2022.01)
*A61B 34/00* (2016.01)
*A61B 90/00* (2016.01)
*G06T 11/00* (2006.01)

(52) U.S. Cl.
CPC ............ *A61B 34/25* (2016.02); *A61B 90/37* (2016.02); *G06T 11/005* (2013.01); *A61B 2090/368* (2016.02)

(58) Field of Classification Search
CPC ............ G06K 9/00; A61B 34/00; A61B 6/00
USPC ........ 382/100, 103, 106–107, 128–132, 154, 382/162, 168, 173, 181, 189, 199, 219, 382/224, 254, 276, 286–291, 305, 312, 382/321; 378/4, 21, 62, 63; 600/424; 623/17.11
See application file for complete search history.

(56) References Cited

U.S. PATENT DOCUMENTS

| | | | |
|---|---|---|---|
| 2010/0041985 A1* | 2/2010 | Simon | A61B 6/463 378/62 |
| 2015/0085981 A1* | 3/2015 | Siewerdsen | A61B 90/37 378/63 |
| 2016/0374764 A1* | 12/2016 | Kemp | A61B 34/20 600/424 |
| 2017/0165008 A1* | 6/2017 | Finley | A61B 6/4441 |
| 2018/0074595 A1 | 3/2018 | Isaacs | |

(Continued)

FOREIGN PATENT DOCUMENTS

| | | |
|---|---|---|
| WO | 2021055522 A1 | 3/2021 |
| WO | 2021061924 A1 | 4/2021 |
| WO | 2021061960 A1 | 4/2021 |

OTHER PUBLICATIONS

International Search Report and Written Opinion dated Oct. 21, 2022 for International Application No. PCT/US2022/036533.

(Continued)

*Primary Examiner* — Seyed H Azarian

(57) ABSTRACT

Imaging systems and methods may facilitate positioning an imaging device in a procedure room. A 3D image of a subject may be obtained, where the subject is to have a procedure performed thereon. A view of the 3D image of the subject may be adjusted to a desired view and an associated 2D image reconstruction at the desired view may be obtained. A position for the imaging device that is associated with the desired view of the 3D image of the subject may be identified. Adjusting a view of the 3D image to a desired view and obtaining a 2D image reconstruction may be performed pre-procedure, such that a user may be able to create a list of desired views pre. A user may adjust a physical position of the imaging device to obtain reconstructed 2D preview images at the adjusted physical position of the imaging device prior to capturing an image.

18 Claims, 7 Drawing Sheets

(56) References Cited

U.S. PATENT DOCUMENTS

2018/0092699 A1* 4/2018 Finley .................. A61B 34/20
2023/0127917 A1* 4/2023 Kim ...................... G06T 17/00
　　　　　　　　　　　　　　　　　　　　　　623/17.11

OTHER PUBLICATIONS

Malik, "Three Dimensional Conformal Radiation Therapy", 76 Pages, Jun. 6, 2017 [https://www.slideshare.net/DeepikaMalik8/three-diemensional-conformal-radiation-therapy] Retrieved Oct. 31, 2022.

"Beam's Eye View", Wikipedia, 2 Pages, XP055970466, Jan. 13, 2021 [https://en.wikipedia.org/w/index.php?title=Beam's_eye_view&oldid=1000053694] Retrieved Oct. 10, 2022.

"Image-guided Radiation Therapy", Wikipedia, 8 Pages, XP055970480, Jan. 1, 2021 [https://en.wikipedia.org/w/index.php?title=Image-guided_radiation_therapy&oldid=997631693] Retrieved Oct. 12, 2022.

"ExacTrac Version 6.0 Klinisches Benutzerhandbuch, Band 1/2 Auflage 1.3", Brainlab, pp. 1-400, Dec. 31, 2013, XP055970532 [https://www.manualslib.de/download/774938/Brainlab-Exactrac-Version-6-0.html] German Only.

* cited by examiner

SYSTEMS AND METHODS FOR SURGICAL NAVIGATION

BACKGROUND

A wide variety of medical devices and navigation systems have been developed for medical use. Some of the devices and systems include visualization devices, implantable devices, surgical tools, and the like. These devices are developed and manufactured by any one of a variety of different methods and may be used according to any one of a variety of different methods. Of the known medical devices and navigation systems, each has certain advantages and disadvantages.

SUMMARY

This disclosure is directed to several alternative designs for, devices of, and methods of surgical navigation. Although it is noted that surgical navigation approaches and systems are known, there exists a need for improvement to those approaches and systems.

Accordingly, one illustrative instance of the disclosure may include a method for use with an imaging system, the method comprising adjusting a view of a three-dimensional image of a subject to a desired view of the three-dimensional image, obtaining a two-dimensional image reconstruction from the three-dimensional image of the subject at the desired view, and identifying a physical position for a physical imaging device that is associated with the desired view.

Additionally or alternative to any of the embodiments in this section, the method further comprises providing instructions, in real time, for moving the physical imaging device to the physical position for the physical imaging device that is associated with the desired view.

Additionally or alternative to any of the embodiments in this section, the method further comprises providing control signals to adjust a location of the physical imaging device to the physical position for the physical imaging device that is associated with the desired view.

Additionally or alternative to any of the embodiments in this section, wherein adjusting the view of the three-dimensional image of the subject to the desired view of the three-dimensional image includes adjusting a position of one or both of the three-dimensional image of the subject and a virtual imaging device to a desired position relative to the other of the three-dimensional image of the subject and the virtual imaging device.

Additionally or alternative to any of the embodiments in this section, the method further comprises identifying a position address for the three dimensional image of the subject at the desired view, and wherein the position for the physical imaging device associated with the desired view is based on the position address.

Additionally or alternative to any of the embodiments in this section, the method further comprises adjusting the view of the three-dimensional image of the subject to a plurality of desired views, obtaining two-dimensional images from the three-dimensional image of the subject at each of the plurality of desired views, identifying a position address of the three-dimensional image of the subject at each of the plurality of desired views, and storing the identified position addresses of the three-dimensional image of the subject.

Additionally or alternative to any of the embodiments in this section, the method further comprises identifying positions for the physical imaging device that are associated with each of the plurality of desired views.

Additionally or alternative to any of the embodiments in this section, wherein the adjusting the view of the three-dimensional image of the subject to the desired view is in response to adjusting a position of the physical imaging device.

Additionally or alternative to any of the embodiments in this section, the method further comprises registering position addresses of the three-dimensional image with positions of the physical imaging device.

Additionally or alternative to any of the embodiments in this section, wherein registering position addresses of the three-dimensional image with positions of the physical imaging device comprises: obtaining a first image of the subject from the physical imaging device at a first location of the physical imaging device, obtaining a second image of the subject from the physical imaging device at a second location of the physical imaging device, comparing the first image of the subject and the second image of the subject to the two-dimensional image reconstruction from the three-dimensional image of the subject; and associating the position addresses of the three-dimensional image with the positions of the physical imaging device based on the first location, the second location, and the comparison of the first image of the subject and the second image of the subject to the two-dimensional image reconstruction from the three-dimensional image of the subject.

Additionally or alternative to any of the embodiments in this section, wherein the physical imaging device is a two-dimensional imaging device and the three-dimensional image is obtained from a three-dimensional physical imaging device.

Additionally or alternative to any of the embodiments in this section, the method further comprising: obtaining a two-dimensional image with the physical imaging device positioned at or proximate to the position, and providing the two-dimensional image for use by a surgeon during a spinal fusion procedure.

Another illustrative instance of the disclosure may include a system comprising a user interface including a display, an imaging device, and a controller coupled to the imaging device and the user interface. The controller is configured to store data related to one or more images of a subject and is programmed to: adjust a view of a three-dimensional image of a subject on the display to a desired view having an associated three-dimensional address, create a synthetic image from the three-dimensional image of the subject at the desired view, and obtain a captured image from the imaging device, wherein the captured image is configured to have a view of the subject that matches a view of the subject in the synthetic image.

Additionally or alternative to any of the embodiments in this section, wherein the controller is further programmed to: associate a position for the imaging device with the three-dimensional address, the associated position for the imaging device is configured to result in the captured image having the view of the subject that matches the view of the subject in the synthetic image.

Additionally or alternative to any of the embodiments in this section, wherein the adjusting the position of the three-dimensional image of the subject on the display to the desired view is in response to adjusting a position of the imaging device.

Additionally or alternative to any of the embodiments in this section, wherein the adjusting the position of the three-dimensional image of the subject to the desired view is in response to receiving user interaction over the user interface.

Additionally or alternative to any of the embodiments in this section, wherein the controller is further programmed to provide at least one output selected from the following outputs: instructions, in real time, for moving the imaging device to a position for taking the captured image that results in the captured image having the view of the subject that matches the view of the subject in the synthetic image, and control signals to move the imaging device to the position for taking the captured image that results in the captured image having the view of the subject that matches the view of the subject in the synthetic image.

Another illustrative instance of the disclosure may include computer readable medium having stored thereon in a non-transitory state a program code for use by a computing device. The program code causing the computing device to execute a method to assist in capturing images during surgery on a subject, the method comprising: selecting a synthetic image of a subject from one or more stored synthetic images of the subject, the synthetic image is associated with an address of a three-dimensional image of the subject, identifying a position for an imaging device that is associated with the address of the three-dimensional image of the subject, and causing the imaging device to capture an image from the position for the imaging device that is associated with the address of the three-dimensional image of the subject.

Additionally or alternative to any of the embodiments in this section, wherein the method further comprises providing at least one of: instructions, in real time, for moving the imaging device to the position for the imaging device that is associated with the address of the three-dimensional image of the subject, and control signals to move the imaging device to the position for the imaging device that is associated with the address of the three-dimensional image of the subject.

Additionally or alternative to any of the embodiments in this section, wherein the method further comprises adjusting a position of the three-dimensional image of a subject to the address of the three-dimensional image in response to one or both of movement of the imaging device and user interactions with a user interface.

The above summary of some example embodiments is not intended to describe each disclosed embodiment or every implementation of the disclosure.

BRIEF DESCRIPTION OF THE DRAWINGS

The disclosure may be more completely understood in consideration of the following detailed description of various embodiments in connection with the accompanying drawings, in which.

Figure 1:
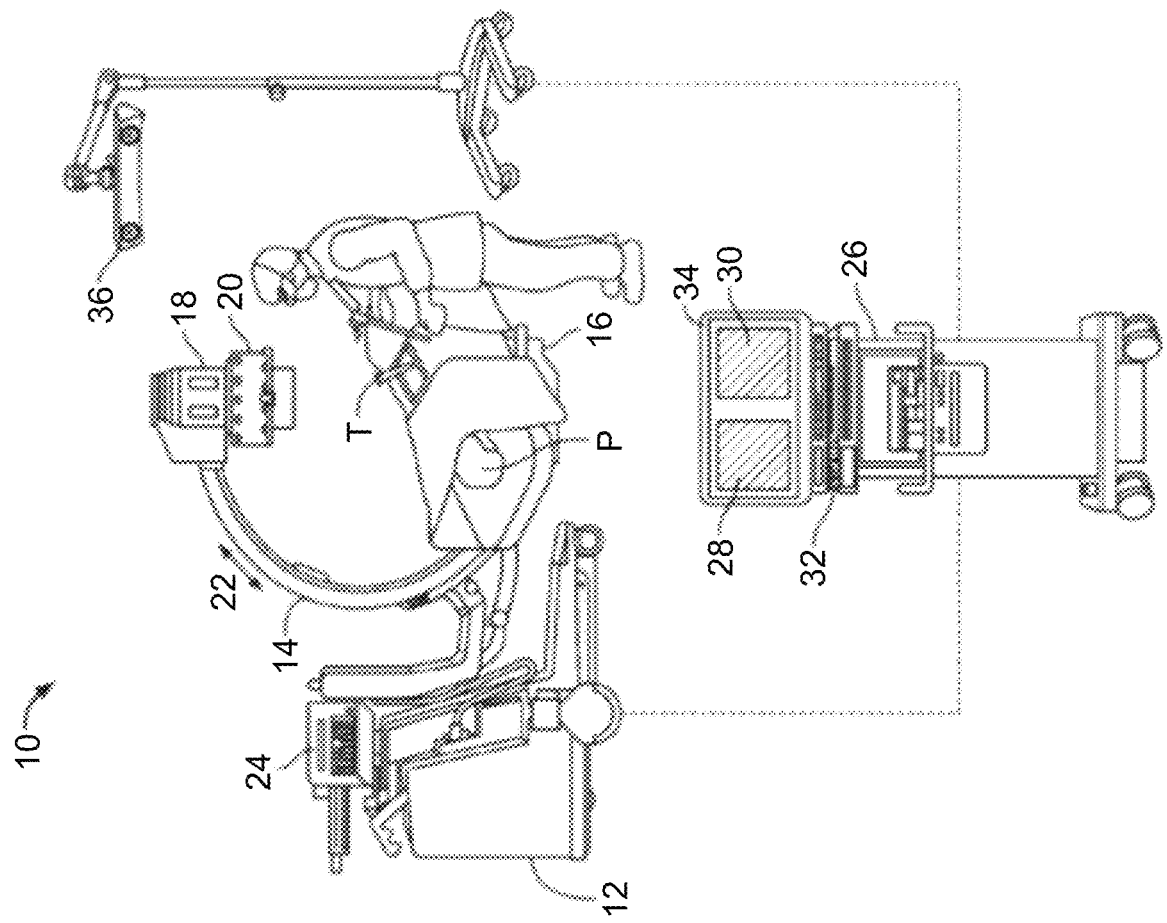
FIG. 1 is a schematic view of an image guided surgical setting.

While the disclosure is amenable to various modifications and alternative forms, specifics thereof have been shown by way of example in the drawings and will be described in detail. It should be understood, however, that the intention is not to limit aspects of the claimed disclosure to the particular embodiments described. On the contrary, the intention is to cover all modifications, equivalents, and alternatives falling within the spirit and scope of the claimed disclosure.

DESCRIPTION

Medical providers (e.g., surgeons, radiologists, etc.) and/or imaging technicians often manually move imaging devices, such as C-arms and/or other suitable imaging devices used during surgeries, to positions that are intended to facilitate obtaining a correct or desired perspective of a subject's anatomy (e.g., a surgical patient's anatomy and/or other suitable anatomy) in a captured image (e.g., an x-ray and/or other suitable image). However, this manual movement is typically done on a trial and error basis without adequate guidance. Taking images with an imaging device on a trial and error basis can be time consuming and problematic as many imaging devices exude radiation when taking images.

For navigation purposes and/or other purposes, surgical spinal procedures often require several images to be captured using an imaging device that emits radiation when capturing images. As such, reducing the number of images that need to be obtained during a surgical spinal procedure has the potential to greatly reduce radiation exposure to the subject and surgical spinal team over time. Similar benefits would be seen with medical procedure teams in other disciplines in which surgical navigation is used.

Virtual techniques may be used to assist medical providers and/or imaging technicians in collecting the desired view of the subject's anatomy. In one virtual technique discussed herein, a view of a three-dimensional (3D) image (e.g., a 3D scan such as a computerized tomography (CT) scan, magnetic resonance image (MRI), etc.) of a subject may be adjusted and/or moved (e.g., panned, tilted, and/or rotated) and a synthetic or reconstruction of a two-dimensional (2D) image may be created from the 3D image at the adjusted view. To facilitate taking several images from different positions of the imaging device, the medical provider may save a single synthetic or reconstructed 2D image or multiple synthetic or reconstructed 2D images (e.g., "images of interest") prior to and/or during a surgery without moving the imaging device and without capturing test images at each imaging device position. The saved synthetic or reconstructed 2D images may be used to either guide the user with on-screen directions on how to move the imaging device to obtain a needed view of the subject and/or to automatically drive the imaging device's position to the correct perspective.

The synthetic or reconstructed 2D image can be used to identify views that a medical provider may want to image during an operation (e.g., a surgery) and position addresses of the 3D image (e.g., coordinates, such as a 3D address (x, y, z) and/or an angular orientation (θ), and/or other suitable addresses) at the identified views may be used to determine positions of the imaging device at which the imaging device may capture images of the subject, where the captured images have a view similar to the view in the synthetic or reconstructed 2D image. Coordinates for the imaging device that are associated with coordinates of the 3D image at identified synthetic or reconstructed 2D images may be obtained or determined once the imaging device is registered to the 3D image of the subject (e.g., once the coordinates of the positioning system of the imaging device are mapped to the coordinates of the 3D image). The registering or mapping between the 3D image and the imaging device may allow for real-time predictions of where to place the imaging device to capture a desired view of the subject and/or real-time predictions of a view of the subject taken from the current position of the imaging device. In some cases, the synthetic or reconstructed 2D image may be utilized as a "preview" of the next image to be taken with the imaging device, and additionally or alternatively, can be updated in real-time as the imaging device moves.

In operation of an illustrative technique to assist a user (e.g., medical providers, imaging technicians, and/or other suitable users) in collecting an image of a desired view of a subject, a user may obtain and/or be presented with a rendering of a 3D image of a subject on a user interface display or screen. Adjacent to the rendering of the 3D image of the subject, a synthetic or reconstructed 2D image of the subject (e.g., a digitally reconstructed radiograph (DRR) and/or other suitable synthetic or reconstructed 2D image) that is based on the view of the 3D image on the user interface and that is produced at least in part from the 3D image may be displayed. The view of the synthetic or reconstructed image may be changed by adjusting the view of the 3D image (e.g., by adjusting one or both of the 3D image and a virtual imaging device relative to one another) to find specific views the user would like to see or capture during a procedure. Then, position addresses of the imaging device corresponding to the specific views they desire to see during the procedure may be saved for access during a procedure to streamline moving the imaging device to location that will produce desired views of the subject. Although not required, a position address (e.g., coordinates, such as a 3D address (x, y, z) and/or angular orientation, and/or other suitable position address) for the 3D image at a desired view, the synthetic or reconstructed 2D image at the desired view, and/or a position address for the imaging device may be saved for each desired view. Such a technique may allow for a list of "images of interest" to be obtained during procedure preparation or even mid-procedure, which will save time during a procedure and reduces radiation exposure for everyone in the procedure room due to mitigating a number of test shots that need to be taken in the procedure room.

During a surgical procedure (e.g., a surgical spinal procedure and/or other suitable surgical procedure), directions on how to position the imaging device in order to capture desired views may be provided via a user interface (e.g., directions on a screen or display, audio directions, etc.). In one example, directions or instructions for manually moving the imaging device may be provided. When the instructions or directions for moving the imaging device are provided on a screen or display, one or more graphical indicators (e.g., arrows, sliders, etc.) and/or text may be provided on the screen or display to show how to move the imaging device to capture an image of the desired view.

Alternatively or additionally, the imaging devices may be driven to imaging device position addresses associated with desired views. For example, the imaging device may be, automatically and/or in response to receiving user input, driven to a position for a next or selected desired view from a list of pre-determined desired views.

Further, a user may be able to adjust the imaging device before and/or during a procedure and view the 3D image and/or the synthetic or reconstructed 2D images of the subject as the imaging device position is adjusted. This real-time manipulation of the imaging device and resulting views of the 3D image and/or synthetic or reconstructed views of potential images may allow for fine adjustments to an image of interest previously saved or otherwise identified.

Turning to the figures, FIG. 1 depicts an illustrative imaging system 10 (e.g., an image navigation system and/or other suitable imaging system). The imaging system 10 may include a base unit 12 supporting an imaging device 14 (e.g., a physical imaging device, such as a C-arm and/or other suitable physical imaging device). The imaging device 14 may be configured to use one or more imaging modalities. Examples of the imaging modalities include, but are not limited to, X-ray, computerized tomography (CT), magnetic resonance imaging (MRI), ultrasound, positron emission tomography (PET), single-photon emission computed tomography (SPECT), optical coherence tomography (OCT), fluorescence imaging, fluoroscopic imaging, and infrared imaging.

When the imaging device 14 is a C-arm and/or a different suitable imaging device requiring radiation, the imaging device 14 may include a radiation source 16 that is configured to be positioned at any orientation with respect to the patient P (e.g., beneath, above, and/or to the side of the patient P) and that directs a radiation beam toward a receiver 18. In some cases, the radiation beam emanating from the radiation source 16 may be conical and the field of exposure may be varied by moving the radiation source 16 closer to or away from the patient P (and/or the receiver 18). Although not required, the radiation source 16 may include a collimator that is configured to restrict the field of radiation.

The imaging device 14 may be rotated about the patient P in the direction of arrow 22 and/or other suitable directions, for different viewing angles of the procedural site (e.g., surgical site, etc.) In some instances, implants or instruments T may be situated at the procedural site, necessitating a change in viewing angle from an unobstructed view of the site. As such, the position of the receiver 18 relative to the patient P, and more particularly relative to the procedure site of interest, may change during a procedure as needed by the medical provider.

The imaging device 14 may be configured to be tracked in one or more suitable manners. Example tracking techniques include, but are not limited to, a local global positioning system (GPS) tracking system, infrared tracking system, radio-frequency object-tracking systems, laser rangefinder systems, etc. In one example, the receiver 18 may include a tracking target 20 mounted thereto that allows for tracking of the position of the imaging device 14 using a tracking device 36. By way of example only, the tracking target 20 may include one or more infrared reflectors or emitters spaced around the target, while the tracking device 36 is configured to triangulate the position of the receiver 18 in a coordinate system from the infrared signals reflected or emitted by the tracking target 20.

The base unit 12 may include a control panel 24 through which a user may control the location of the imaging device 14, as well as an amount of radiation exposure from the radiation source 16. An illustrative control panel 24 may permit the user to "shoot a picture" of the procedural site when desired (e.g., a radiology technician may initiate a picture in response to a medical provider's request), control the radiation dose, and initiate a radiation pulse image.

In operation, once an image has been shot by the imaging device 14, the receiver 18 may transmit image data to an image processing device 26. The image processing device 26 may be separate from, at least partially integrated with, or entirely integrated with the base unit 12, the imaging device 14, the control panel 24, and/or a remote computing device (e.g., a server and/or other remote computing device), as desired.

The image processing device 26 may include memory (e.g., digital memory and/or other suitable memory) associated therewith and a processor for executing digital and/or software instructions. The image processing device 26 may also incorporate a frame grabber that uses frame grabber technology to create a digital image for projection as displays 28, 30 on a display device 34. Although two displays 28, 30 are depicted in FIG. 1, the display device 34 may have a single display, two displays, or more than two displays, as desired. Moreover, each display may have any suitable number of panes for separating information and/or views on the display.

The displays 28, 30 of the display device 34 may be positioned for interactive viewing by a user during a procedure. In one instance, one of the displays 28, 30 may be utilized to display a first image of a subject and the other one of the displays 28, 30 may be utilized to display a second image of the subject. For example, a first display may show a lateral view of the subject and a second display may show an anterior/posterior (A/P) view of the subject, the first display may show a baseline image of the subject at the procedure site and the second display may show a current scan of the subject at the procedure site, the first display may show a current scan of the subject at the procedure site and the second display may show a "merged" scan based on a prior baseline scan and a low radiation current scan (e.g., as described in U.S. application Ser. No. 15/379,245 filed on Dec. 14, 2016 and titled 3D VISUALIZATION DURING SURGERY WITH REDUCED RADIATION EXPOSURE, which is hereby incorporated by reference in its entirety for any and all purposes), the first display may show a 3D image of a subject and the second display may display a DRR image based on the 3D image of the subject, or the first display and/or the second display may show other images and/or other suitable combinations of images thereon.

The image processing device 26 may include one or more input devices 32. Example input devices include, but are not limited to, keyboards, touch screens, a mouse, a touch pad, a microphone, etc. In some cases, the input device 32 may allow a user to select and/or manipulate images displayed on the displays 28, 30. The input devices 32 may incorporate one or more keys, buttons, graphical icons, and/or other features corresponding to various tasks and/or features implemented by the image processing device 26.

The image processing device 26 may include a processor that converts the image data obtained from the receiver 18 into a digital format and/or other suitable format. In some cases, the imaging device 14 may be operating in a cinematic exposure mode and generating many images each second. In these cases, multiple images may be averaged together over a short time period into a single image to reduce motion artifacts and noise, but this is not required.

Communication between the base unit 12, the imaging device 14, the control panel 24, the image processing device 26, and/or the tracking device 36 may occur via one or more wired and/or wireless connections. Moreover, communication between devices and/or components of the imaging system 10 may occur over one or more local area networks (LANs) and/or wide area networks (WANs).

Figure 2:
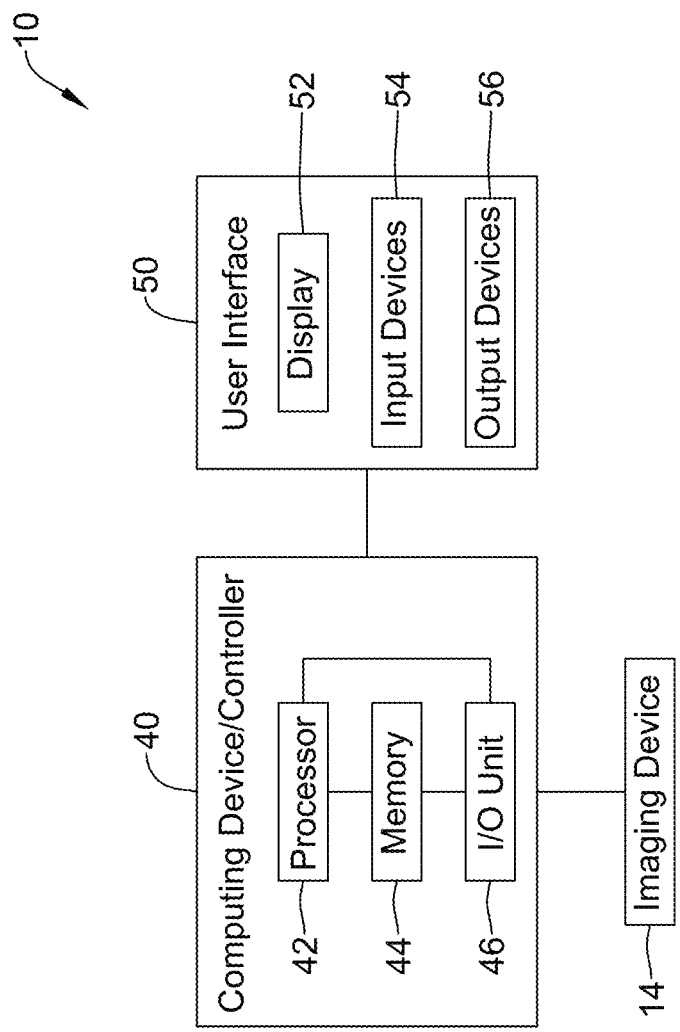
FIG. 2 is a schematic box diagram of an illustrative imaging system.

FIG. 2 depicts a schematic box diagram of the imaging system 10 having a computing device or controller 40, a user interface 50, and the imaging device 14. Although the base unit 12, the control panel 24, the image processing device 26, and the tracking device 36 are not explicitly depicted and labeled in FIG. 2, the imaging system 10 may include these components and/or other suitable components.

The computing device or controller 40 may be any suitable computing device configured to process data of or for the base unit 12, imaging device 14, the control panel 24, the image processing device 26, and/or the tracking device 36. In some cases, at least a portion of the base unit 12, the imaging device 14, the control panel 24, the image processing device 26, and/or the tracking device 36 may be incorporated into the computing device or controller 40 and/or the user interface 50. Further, the base unit 12, the imaging device 14, the control panel 24, the image processing device 26, and/or the tracking device 36 may incorporate one or more computing devices similar to or having components similar to the computing device or controller 40.

The computing device or controller 40 may be configured to facilitate operation of the imaging system 10. The computing device or controller 40, in some cases, may be configured to control the operation of the base unit 12, the imaging device 14, the control panel 24, the image processing device 26, and/or the tracking device 36 by establishing and/or outputting control signals to components of the base unit 12, the imaging device 14, the control panel 24, the image processing device 26, and/or the tracking device 36 to control and/or monitor operation of these units and devices.

In some cases, the controller 40 may communicate with a remote server or other suitable computing device. When the controller 40, or at least a part of the controller 40, is a component separate from a structure of the base unit 12, the imaging device 14, the control panel 24, the image processing device 26, and/or the tracking device 36, the controller 40 may communicate with electronic components of the imaging system 10 over one or more wired or wireless connections or networks (e.g., LANs and/or WANs).

The illustrative controller 40 may include, among other suitable components, one or more processors 42, memory 44, and/or one or more I/O units 46. Example other suitable components of the controller 40 that are not specifically depicted in FIG. 2 may include, but are not limited to, communication components, a touch screen, selectable buttons, a housing, and/or other suitable components of a controller. As discussed above, one or more components of the controller 40 may be separate from the components of the imaging system 10 and/or incorporated into the components of the imaging system 10.

The processor 42 of the controller 40 may include a single processor or more than one processor working individually or with one another. The processor 42 may be configured to receive and execute instructions, including instructions that may be loaded into the memory 44 and/or other suitable memory. Example components of the processor 42 may include, but are not limited to, central processing units, microprocessors, microcontrollers, multi-core processors, graphical processing units, digital signal processors, application specific integrated circuits (ASICs), artificial intelligence accelerators, field programmable gate arrays (FPGAs), discrete circuitry, and/or other suitable types of data processing devices.

The memory 44 of the controller 40 may include a single memory component or more than one memory component each working individually or with one another. Example types of memory 44 may include random access memory (RAM), EEPROM, flash, suitable volatile storage devices, suitable non-volatile storage devices, persistent memory (e.g., read only memory (ROM), hard drive, flash memory, optical disc memory, and/or other suitable persistent memory) and/or other suitable types of memory. The memory 44 may be or may include a non-transitory computer readable medium. The memory 44 may include instructions stored in transitory and/or non-transitory state on a computer readable medium that may be executable by the processor 42 to cause the processor to perform one or more of the methods and/or techniques described herein.

The I/O units 46 of the controller 40 may include a single I/O component or more than one I/O component each working individually or with one another. Example I/O units 46 may be or may include any suitable types of communication hardware and/or software including, but not limited to, communication ports configured to communicate with electronic components of the imaging system 10 and/or with other suitable computing devices or systems. Example types of I/O units 46 may include, but are not limited to, wired communication components (e.g., HDMI components, Ethernet components, VGA components, serial communication components, parallel communication components, component video ports, S-video components, composite audio/ video components, DVI components, USB components, optical communication components, and/or other suitable wired communication components), wireless communication components (e.g., radio frequency (RF) components, Low-Energy BLUETOOTH protocol components, BLUETOOTH protocol components, Near-Field Communication (NFC) protocol components, WI-FI protocol components, optical communication components, ZIGBEE protocol components, and/or other suitable wireless communication components), and/or other suitable I/O units 46.

The user interface 50 may be configured to communicate with the computing device or controller 40 via one or more wired or wireless connections. The user interface may include one or more display devices 52, one or more input devices 54, one or more output devices 56, and/or one or more other suitable features.

The display device 52 may be similar to the display device 34, discussed above, but this is not required. The display device 52 may be any suitable display. Example suitable displays include, but are not limited to, touch screen displays, non-touch screen displays, liquid crystal display (LCD) screens, light emitting diode (LED) displays, head mounted displays, virtual reality displays, augmented reality displays, and/or other suitable display types.

The input device(s) 54 may be and/or may include any suitable components and/or features for receiving user input via the user interface. Example input device(s) 34 include, but are not limited to, touch screens, keypads, mice, touch pads, microphones, selectable buttons, selectable knobs, optical inputs, cameras, gesture sensors, eye trackers, voice recognition controls (e.g., microphones coupled to appropriate natural language processing components) and/or other suitable input devices. In one example, the input devices 54 may include a touch screen that allows for selection of pan, tilt, zoom (PTZ) virtual buttons in or on the display device 52, but this is not required.

The output device(s) 56 may be and/or may include any suitable components and/or features for providing information and/or data to users and/or other computing components. Example output device(s) 36 include, but are not limited to, displays, speakers, vibration systems, tactile feedback systems, optical outputs, and/or other suitable output devices.

Figure 3:
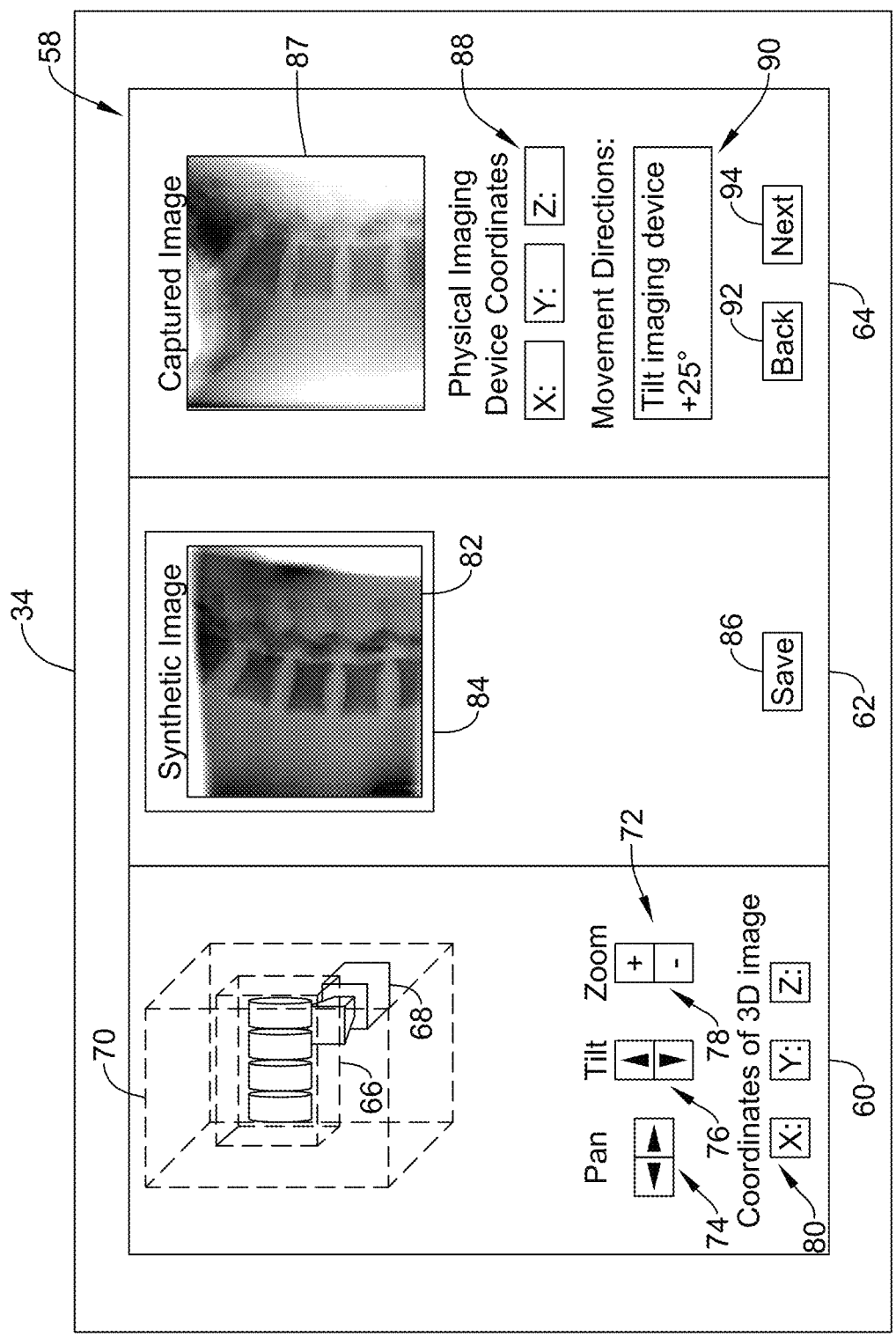
FIG. 3 is a schematic diagram of an illustrative user interface for an imaging system.

FIG. 3 is a schematic view of illustrative screens and/or panes for the display device 34 used with the image processing device 26, as discussed above. The display device 34 may have any suitable number of displays (e.g., the display 28, the display 30, the display device 52, and/or other suitable displays), screens, and/or panes. The display device 34 may be implemented on any suitable type of computing device having a display, including but not limited to a desktop monitor, a laptop, a mobile device, a tablet computing device, etc.

The display device 34 may be a hardware device and the screens may be rendered by the display and are what is presented to the user by the display device 34 (e.g., what the user views). The panes may be subsections of the screens (e.g., separate areas of a split or single screen or window).

As depicted in FIG. 3, the display device 34 may have or display a screen 58 with a first pane 60, a second pane 62, and a third pane 64, but other suitable numbers of screens or panes and combinations of screens and panes are contemplated. Further, each pane may have any suitable dimensions for displaying desired information thereon and, in some cases, the dimensions of the panes may be adjustable.

The first pane 60, as depicted in FIG. 3, may include a 3D image 66 of a subject (e.g., a CT scan of a spine of the subject and/or other suitable 3D image) and a virtual imaging device 68 (e.g., a virtual C-arm device and/or other suitable virtual imaging device) in a 3D viewing space 70 (e.g., a 3D representation of a procedure room and/or other suitable 3D viewing space). Although the 3D image 66 and 3D viewing space 70 may represent 3D objects and provide a sense of depth, they may nonetheless be provided in a 2D form when provided at a 2D display. The virtual imaging device 68 may be an element that is determinative of a view of the 3D image 66 at which a synthetic or reconstructed 2D image of the subject is obtained or produced using the 3D image 66. Positioning of the virtual imaging device 68 relative to the 3D image 66 may simulate a positioning of a physical imaging device (e.g., the imaging device 14 and/or other suitable physical imaging device) relative to a subject (e.g., a patient and/or other suitable subject) in a procedure room. In some cases, a view of the 3D image 66 in the 3D viewing space 70 may be adjustable with respect to the virtual imaging device 68, similar to how the imaging device 14 may be adjustable with respect to the subject in a procedure room. As an alternative to depicting the virtual imaging device 68 in the 3D viewing space 70, the virtual imaging device may be presumed to be located at a location of the viewer such that the view of the 3D image 66 in the 3D viewing space 70 may be a view of the 3D image 66 relative to the virtual imaging device and adjustment of the view of the 3D image 66 would be an adjustment of the 3D image 66 relative to the virtual imaging device 68.

The view of the 3D image 66 of the subject may be adjusted by adjusting one or both of the 3D image 66 and the virtual imaging device 68 with respect to one another in any suitable manner. As depicted in FIG. 3, the first pane 60 may include position adjusting controls 72 configured to be selected by a user and in response to the image processing device 26 receiving the user selection, the relative position of the 3D image 66 and/or the virtual imaging device 68 may be adjusted. In some cases, the adjustments to the relative positioning of the 3D image 66 and the virtual imaging device 68 in the 3D viewing space 70 via the adjusting controls 72 may be reflected by the imaging processing device 26 causing the 3D image 66, the virtual imaging device 68, and/or both of the 3D image 66 and the virtual imaging device 68 to change positions in the 3D viewing space 70.

The position adjusting controls 72 may be any suitable type of controls configured to adjust a view of the 3D image 66 of the subject to one or more desired views of the 3D image (e.g., buttons, sliders, or other user interface elements). Although other controls are contemplated, pan controls 74 (e.g., a set of arrows and/or other suitable pan controls), tilt controls 76 (e.g., a set of arrows and/or other suitable tilt controls), and zoom controls 78 (e.g., zoom in (+) and zoom out (−) controls and/or other suitable zoom controls) are depicted as example controls for adjusting a view of the 3D image 66 of the subject. Further, the view of the 3D image 66 may be adjusted by interacting with the screen 58 via an input device (e.g., the input device 54, such as a mouse, touch pad, touch screen, etc., and/or other suitable input device) to manually move or adjust (e.g., pan, tilt, zoom, etc.) the 3D image 66, the virtual imaging device 68, and/or the 3D viewing space 70.

In some examples, the relative position of the physical imaging device 14 to the patient P controls the relative position of the virtual imaging device 68 relative to the 3D image 66. For example, the position of the physical imaging device 14 can be tracked using the tracking device 36, and as the physical imaging device 14 is moved around the procedure room, the virtual imaging device 68 makes a corresponding move in the virtual space.

The first pane 60 may include position information 80 (e.g., a position address of coordinates, such as a 3D address (x, y, z) and/or angular orientation, and/or other suitable addresses) for the 3D image 66 in the 3D viewing space relative to a coordinate system and/or the virtual imaging device 68. In some cases, the position information 80 may be a position address for the 3D image 66 relative to the virtual imaging device 68 (e.g., a position address for a point or feature in the 3D image relative to the virtual imaging device 68), where the position address is provided as a set of x, y, z coordinates and/or angular orientation (0) for the 3D image 66. Although not required, a coordinate system for the 3D image 66 may be relative to the virtual imaging device 68.

The 3D image 66 may be a 3D data set rendering an image of a subject. The 3D data set may be readily available to the user from pre-procedure scans (e.g., CT scans, MRIs, etc.) and thus, no additional ionizing radiation needs to be introduced to the subject for the techniques described herein. Use of an already existing 3D data set may result in time and cost savings for the user and/or the subject, as acquiring a 3D data set can take time and the cost of obtaining the 3D data set is not negligible. With that said, further scans may be obtained pre-procedure, during a procedure, and/or after the procedure, as desired.

As discussed herein, the 3D data set can be of various image parameters such as field of view, resolution, signal-to-noise ratio, contrast, brightness, and image size. In some cases, the 3D data set can have sufficient image parameters (e.g., at least a field of view) sufficient to view an area of interest of the subject and create synthetic or reconstructed 2D images (e.g., DRR images) of the subject using the 3D data set. In one example for a surgical spinal procedure, a 3D data set may have a field of view of forty (40) centimeters (cm) by forty (40) cm by forty (40) cm in order to cover an anatomy of a lower back of a subject. In this particularly example, the resolution or voxel size may be 0.2 cm by 0.2 cm by 0.2 cm, and the 3D data set may include the complete 3D volume of an anatomical structure that is used to create a synthetic or reconstructed 2D image.

In some cases, the 3D data set may be acquired by one or more imaging modalities. Nonlimiting examples of the imaging modalities include, but are not limited to, X-ray, computerized tomography (CT), magnetic resonance imaging (MRI), ultrasound, positron emission tomography (PET), single-photon emission computed tomography (SPECT), optical coherence tomography (OCT), fluorescence imaging, fluoroscopic imaging, and infrared imaging. The 3D data set may or may not be acquired using the same imaging modality or modalities as the imaging device 14, discussed herein.

In some cases, the 3D data set may or may not be acquired using a projection based imaging modality such that the spatial resolution of the anatomy in the third dimension (e.g., thickness or height of an image voxel) is equal to or greater than a desired resolution. In some instances, the 3D data set utilizes averaging (over multiple time points) or other signal processing methods to generate the 3D data set that can be used by the systems, methods, and media herein. Nonlimiting examples of the other signal processing methods include, but are not limited to, filtering, sampling, translation, rotation, segmentation, registration, and pattern recognition.

In some configurations, the 3D data set may include a plurality of 2D images of the subject, where the 2D images are stacked in a third direction that is not parallel to the 2D images. In some configurations, the 3D data set may include a 3D volume image of the subject, in particular, of an anatomical region on which the procedure is to be performed.

The second pane 62 of the screen 58 may be configured to display an obtained 2D image 82 in a 2D image space 84, where the 2D image 82 is reconstructed or synthetically produced from the 3D image 66 of the subject (e.g., produced using DRR techniques and/or other suitable techniques) from the perspective represented by the virtual imaging device 68 at the view of the 3D image represented in the first pane 60. In some cases, the 2D image 82 depicted in the 2D image space 84 may be updated in real time after adjusting the 3D image to a desired view and/or adjusting a position of the imaging device 14 (e.g., as discussed in greater detail below). The term "real time", as used herein, is intended to mean virtually immediately such that there is recognizable feedback in response to an input (e.g., input such as a user selection of a button, an adjustment of a view of the 3D image, an adjustment of the imaging device 14, etc.)

The second pane 62 may include one or more buttons or selectable features. In one example, the second pane 62 may include a save button 86 for a user to select to save the 2D image 82 displayed. In response to receiving a user selection of the save button 86 or other user input intended to cause the 2D image 82 to be saved, the image processing device 26 may store the displayed synthetic or reconstructed 2D image 82 in a local or remote 2D image database. In some cases, the position address (e.g., a set of coordinates) for a view of the 3D image 66 used to produce the 2D image 82 may be saved or stored with the 2D image 82. In some cases, a plurality of desired 2D images 82 and associated coordinates for the 3D image 66 may be saved as a list of views (e.g., a list of "images of interest") that are desired to be obtained using the imaging device 14 during a procedure.

The synthetic or reconstructed 2D image 82 may be a projection image that contains a projection of anatomical structure from a 3D image of the subject (e.g., the 3D image 66 and/or other suitable 3D image). In other words, the 2D image 82 may be formed from summing an intensity along all points in the 3D image along a perspective path for each 2D image pixel (e.g., from a view of the 3D image 66 relative to a position of the virtual imaging device 68).

As discussed herein, the 2D image 82 can be of or have various image parameters such as field of view, resolution, signal-to-noise ratio, contrast, brightness, and image size. In some cases, the 2D image 82 can have sufficient image parameters (e.g., at least a field of view) sufficient to view an area of interest of the subject. In one example, the 2D image 82 may have a field of view of forty (40) cm by forty (40) cm in order to cover an anatomy of a lower back of a subject. In this particular example, the resolution or pixel size may be 0.5 cm by 0.5 cm. In another example, the image resolution or pixel size is at or less than 1 millimeter (mm), e.g., 0.5 mm by 0.5 mm.

The third pane 64 may depict information related to a position of the imaging device 14 that is associated with a desired view of the 3D image 66 of the subject and at which an image from the imaging device 14 is intended to match the 2D image 82 at the desired view of the 3D image 66. Alternatively or additionally, the third pane 64 or an additional pane may depict information related to a current position of the imaging device 14.

The position information may provide any suitable position information related to the positioning of the imaging device 14. Example position information includes, but is not limited to, a position address 88 (e.g., a set of coordinates, such as a 3D address of x, y, z coordinates and/or angular orientation coordinates, and/or other suitable addresses) for the imaging device 14 that is associated with the view of the 3D image 66 and/or the displayed 2D image 82, directions on how to move the imaging device 14 to the position address 88, a 2D image 87 captured by the imaging device 14 at the position address 88, and/or other suitable information related to a position of the imaging device 14. The position address 88, the captured 2D image 87, and/or the movement instructions 90 may be updated in real time as the 3D image 66 is adjusted, as the synthetic or reconstructed 2D image 82 is updated, as the imaging device 14 moves, and/or in response to a user selection of a 2D image or a desired view of the 3D image.

In one example of providing directions on how to move the imaging device 14 to the position address 88, the image processing device 26 may output movement instructions 90 for manually adjusting a position of the imaging device 14 to obtain an image that is intended to match (e.g., exactly match or substantially match) the depicted 2D image 82. In some cases, the movement instructions 90 may be updated in real time as the imaging device 14 moves, but this is not required. Alternatively or additionally to providing directions on how to move the imaging device 14 to the position address 88, when the imaging device 14 is an automated imaging device 14, the image processing device 26 may output or may facilitate outputting control signals to the imaging device 14 that are configured to adjust the imaging device 14 to the position address (e.g., the coordinate set) associated with the desired view of the 3D image.

In some cases, the third pane 64 may include one or more selectable buttons. Example buttons include a next button, a back button, a select button, a capture button for initiating a capture of an image with the imaging device, and/or other suitable selectable buttons. In the example third pane 64 depicted in FIG. 3, a selectable back button 92 and a selectable next button 94 are depicted, which may be selected by a user to move between views of the 3D image and/or the synthetic or reconstructed 2D views that are saved in a list of views (e.g., a list of "images of interest") of the 3D/2D images. Such list of images may be identified and saved in a list prior to a procedure using the imaging device 14 and/or during a procedure and the user may use the selectable buttons 92, 94 to move through the images of the list during a procedure. In some cases, the image processing device 26 may update the position address 88 and/or the movement directions 90 in real time in response to receiving user input selecting the back button 92 and/or the next button 94. Selecting a select button (not shown) may initiate updating movement directions 90 and/or imaging device coordinates 88 for a current view the list of views.

Once the imaging device 14 is at the desired position address, an image of the subject may be captured by the imaging device 14. In some cases, the captured 2D image 87 may be displayed on the screen 58 (e.g., in the third pane 64 and/or in one or more other suitable pane). Displaying the captured 2D image 87 on the screen 58 may allow a user to compare the captured 2D image to the synthetic or reconstructed 2D image 82 associated with the position address 88 of the imaging device 14.

As an alternative to or in addition to updating the information on the screen 58 (e.g., in the panes 60, 62, 64) in response to relative positioning of the 3D image 66 and the virtual imaging device 68 or selecting views from a list of views, the information on the screen 58 may be updated in response to movement of the imaging device 14. In some cases, the information on the screen 58 may be updated in real time in response to movement of the imaging device 14, but this is not required. In one example, as a position of the imaging device 14 is adjusted, the imaging device coordinates 88, the synthetic or reconstructed 2D image 82, the 3D image coordinates 80, the relative positioning of the 3D image 66 and the virtual imaging device 68, and/or other suitable information may be updated in real time to reflect the adjusted position of the imaging device 14.

Figure 4:
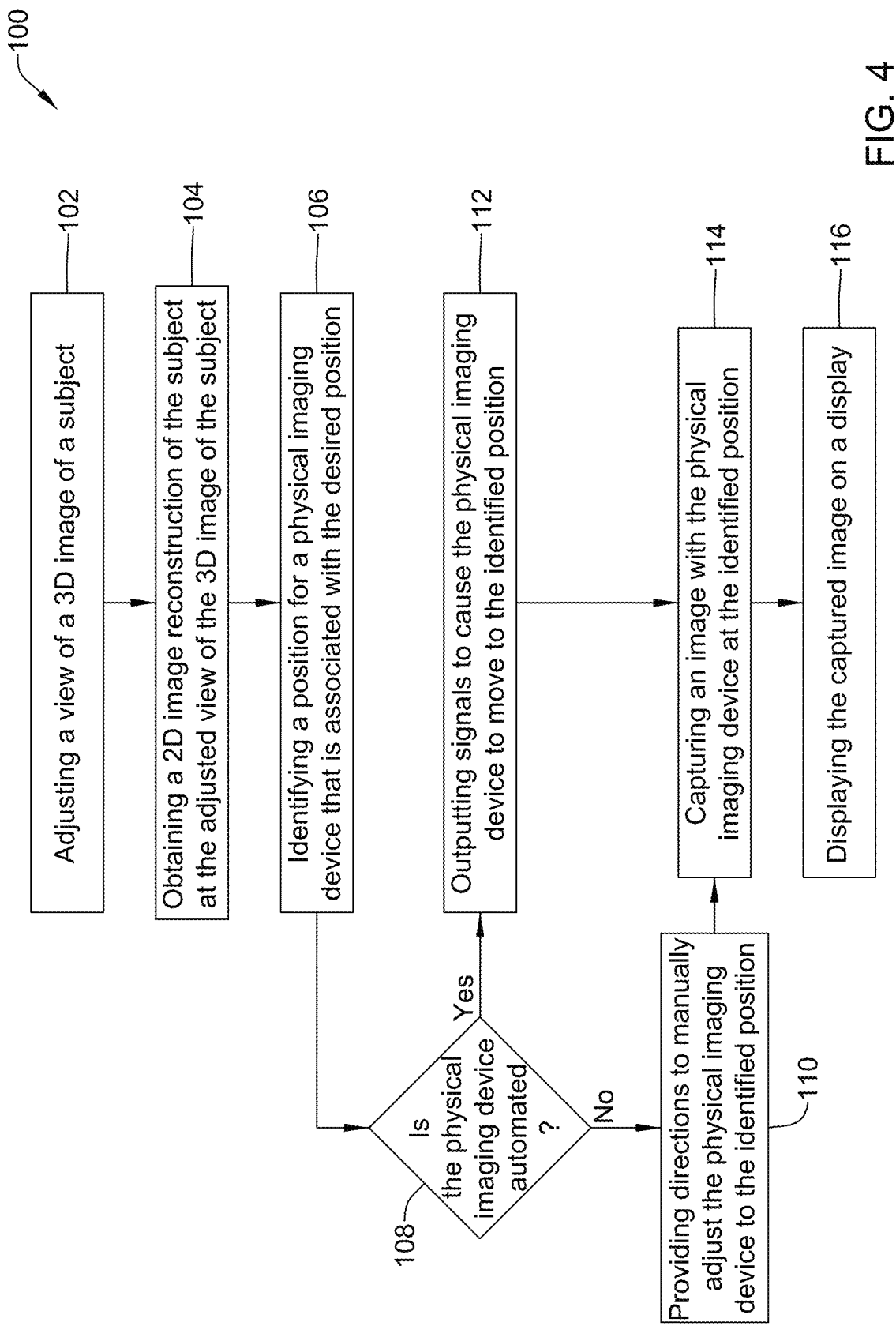
FIG. 4 is a schematic diagram of an illustrative method for use with an imaging system.

FIG. 4 schematically depicts an illustrative method 100 for use with an imaging system (e.g., the imaging system 10 and/or other suitable imaging system). In some cases, the method 100 may be utilized to facilitate determining positions of a physical imaging device (e.g., the imaging device 14 and/or other suitable types of physical imaging devices) to obtain desired views of a subject during a procedure on the subject, while mitigating radiation exposure to those in the procedure room.

The method 100 may utilize a 3D image or data set (e.g., the 3D image 66 and/or other suitable image) of a subject that is obtained from a 3D scan of the subject prior to or during a procedure to be performed on the subject. Once the 3D image or data set has been obtained, the data may be further obtained by or uploaded to a computing device (e.g., the computing device or controller 40 and/or other suitable computing device) and the 3D image or data set may be registered or mapped with the physical imaging device configured to image the subject during the procedure. The registering of the 3D image or data set may be performed in a manner similar to as discussed herein (e.g., see the discussion below with respect to FIG. 7) and/or in one or more other suitable manners. Alternatively or additionally, the 3D image and/or data set may have already been registered with the physical imaging device prior to and/or at the time of obtaining the 3D image or data set.

Once the 3D image or data set of the subject has been obtained, the method 100 may move to adjusting 102 a view of the 3D image of the subject to a desired view of the 3D image, where a position address of the 3D image or data set may be identified and associated with the desired view of the 3D image or data set. The adjusting the view of the 3D image of the subject to a desired view of the 3D image may occur in any suitable manner. In one example, adjusting the view of the 3D image of the subject to a desired view may include adjusting a position of the 3D image of the subject relative to a virtual imaging device, adjusting a position of the virtual imaging device relative to the 3D image, and/or adjusting the 3D image and the virtual imaging device relative to one another. Further, the computing device may receive user input via a user interface (e.g., the user interface 50 and/or other suitable user interface) and in response to receiving the user input, the computing device may adjust the view of the of the 3D image or data set of the subject to the desired view as instructed. In some cases, the computing device may adjust the view of the 3D image or data set of the subject to a desired view in response to movement of the physical imaging device.

Once or as a view of the 3D image or data set of the subject is adjusted to a desired view, a 2D image reconstruction (e.g., the synthetic or reconstructed 2D image 82 and/or other suitable reconstructed 2D image) may be obtained 104 from the 3D image or data set of the subject at the desired view. The obtained 2D image reconstruction is intended to mimic or provide a prediction of a 2D image obtained from the physical imaging device if the physical imaging device were imaging the 3D image or data set at the desired view. When the 3D image or data set of the subject is a CT scan, the 2D image reconstruction may be a DRR image and obtained using known techniques for producing digitally reconstructed radiograph images.

In operation, a user may view the 2D image reconstruction to determine if the 3D image is at a desired view useful for the procedure or other purposes. If the 2D image reconstruction is not a useful view, the system can receive, from the user, further adjustments to the 3D image until the 2D image reconstruction depicts a view useful to the user. Thus, a desired view of the 3D image may be any suitable view that results in a 2D reconstruction view that is useful to a user during a procedure.

Although not required, the obtained 2D image reconstruction may be saved in memory along with a position address of the 3D image or data set associated with the desired view of the 3D image. Further, features 102 and 104 of the method 100 may be repeated for a plurality of desired views and a list of position addresses for the plurality of desired views of the 3D image or data set may be saved or otherwise stored with associated 2D image reconstructions for the 3D image at the plurality of desired views. In some cases, the list of position addresses for the plurality of desired views may represent views of the subject that the user expects to be useful during a procedure on the subject.

Further, the method 100 may include associating or identifying 106 a position for the physical imaging device that is associated with the desired view of the 3D image or data set. For example, when a positioning of the 3D image or data set is mapped or registered with positioning of the physical imaging device relative to the subject, a position (e.g., a position address, such as a set of coordinates) for the physical imaging device may be identified that is associated with the desired view of the 3D image (e.g., where the position for the physical imaging device associated with the desired view may be based on the position address of the 3D image associated with the desired view). For example, the registration between a physical space in the operating room and the 3D space can be used as a map that converts the position of the virtual imaging device to a desired position of the physical imaging device in the operating room. Registration techniques are described in more detail in reference to FIG. 7. As discussed, the desired view of the 3D image may be a view that is associated with a view of the subject that a user may want to view during a procedure and the associated or identified position of the physical imaging device that is associated with the desired view of the 3D image or data set may be configured to result in a captured image at the associated or identified position having a view of the subject that matches (e.g., exactly matches or substantially matches) the view of the subject in the 2D image reconstruction of the subject at the desired view of the 3D image or data set. Although not depicted in FIG. 4 and not necessarily required, the position (e.g., the position address or set of coordinates) for the physical imaging device may be saved in memory along with the coordinates for the 3D image and/or the 2D image reconstruction.

In some cases, the identifying 106 a position for the physical imaging device may occur at some delayed time (e.g., during a procedure) after a time of (e.g., a time prior to the procedure) adjusting 102 a view of the 3D image or data set of the subject to the desired view and obtaining 104 the 2D digital image reconstruction from the 3D image at the desired view. Alternatively or additionally, when the 3D image or data set is registered with the imaging device, identifying 106 the position of the physical imaging device that is associated with or otherwise based on the desired view of the 3D image or data set may be done in real time in response to selecting a desired view, accepting the obtained 2D image reconstruction of the 3D image or data set at the desired view, and/or in response to one or more other suitable user inputs. Further, identifying 106 the position of the physical imaging device that is associated with or otherwise based on the desired view of the 3D image or data set may be done in real time in response to movement or an adjusted position of the physical imaging device, such that the position address of the 3D image or data set at the desired view, the 2D image reconstruction at the desired view, and the position for the physical imaging device may all be determined simultaneously or substantially simultaneously.

A determination 108 may be made as to whether the imaging device is automated (e.g., is capable of automated movement in response to control signals). For example, a processor can query a data structure storing information about the capabilities of the imaging device, such as whether the imaging device is automated. As another example, the system can prompt the user to provide information regarding whether the imaging device is automated.

When the imaging device is determined to not be automated, the computing device may provide 110 or otherwise output directions or instructions via the user interface (e.g., written instructions via a display, audio instructions via speaker, etc.) for a user to manually adjust the imaging device to the identified position (e.g., the identified coordinates) associated with the desired view of the 3D image. Although not required, the instructions may be provided in real time. For example, in response to identifying the position for the physical imaging device and determining the physical imaging device is not configured for automated movement, instructions may be automatically provided for moving the imaging device to the position for taking an image with the physical imaging device. If the instructions include several sequential steps, all of the instructions may be initially provided or a next instruction may be provided after the computing device receives an indication (e.g., an automated indication or user-initiated indication) that current instruction has been completed.

When the imaging device is determined to be automated, the computing device may output 112 control signals to cause the physical imaging device to move to the identified position (e.g., the identified coordinates) associated with the desired view of the 3D image. Although not required, the outputted control signals may be provided in real time. For example, in response to identifying the position for the physical imaging device and determining the physical imaging device is configured for automated movement, control signals may be automatically provided to cause the physical imaging device to move to the identified position. Alternatively or additionally, the control signals may be initiated upon receipt of user input. Depending on how the physical imaging device is automated, the computing device can, for example, provide the physical imaging device with a target coordinate to move to. In another example, the computing device can use a control loop (e.g., a PID controller) to send move signals to the physical imaging device based on a difference between its current position and the desired position. In some examples, the imaging device is partially automated (e.g., the tilt and zoom being automated and the x-y position of the imaging device in the procedure room being controlled by a user). In such instances, the automated portion can be controlled automatically and the user can be instructed to manually perform the rest of the adjustments.

Once the physical imaging device has been moved to the identified position, the physical imaging device may obtain or capture 114 an image from the identified position. For example, the computing device can send a signal to cause the imaging device to obtain an image. In another example, the computing device can prompt a user that the physical imaging device is properly positioned and instruct the user to obtain the image. The captured image from the identified position may be configured to have a view of the subject that matches a view of the subject in the 2D image reconstruction. The captured image may match the view of the subject in the 2D image reconstruction when the captured image is the same as or is substantially the same as the view of the subject in the 2D image reconstruction.

Although this is not required, a computer vision algorithm may be utilized to compare the captured image to the 2D image reconstruction. For example, the computer vision algorithm can be configured to subtract one image from another and provide a score or value associated with the level of difference between the images (e.g., using mean squared error). Another example algorithm is an algorithm that implements the structural similarity index measure. When the computer vision algorithm determines the captured image does not match the 2D image reconstruction, instructions and/or control signals may be determined for adjusting the physical imaging device to capture a further image that is configured to match the view of the subject in the 2D image reconstruction.

Further, the registration or mapping between the 3D image or data set and the physical imaging device may be updated, in real time or otherwise, in response to each image or set of images (when a burst of images are captured) that are captured or obtained. For example, an algorithm can identify the relative change in one or more landmarks (e.g., anatomical landmarks or implants) from one set of images to another and then modify the mapping to account for these changes. For example, the modifications can be performed using an iterative optimization algorithm to reduce an error in the current mapping. Such updating of the registration or mapping may assist in accounting for position changes of the physical imaging device relative to the subject over time and/or errors in the registration or mapping.

When automated, the physical imaging device may automatically capture an image once it is positioned at the identified position. However, this is not required and the imaging device may capture the image in response to a computing device (e.g., the base unit 12, the imaging device 14, the control panel 24, the image processing device 26, and/or other suitable computing device) receiving a user interaction therewith indicating an image should be captured with the imaging device. After capturing an image, the captured image may be displayed 116 or otherwise provided on a display for processing and/or for a user (e.g., a surgeon, radiologist, and/or other suitable medical provider) to view during a procedure (e.g., a surgery and/or other suitable medical procedure).

Figure 5:
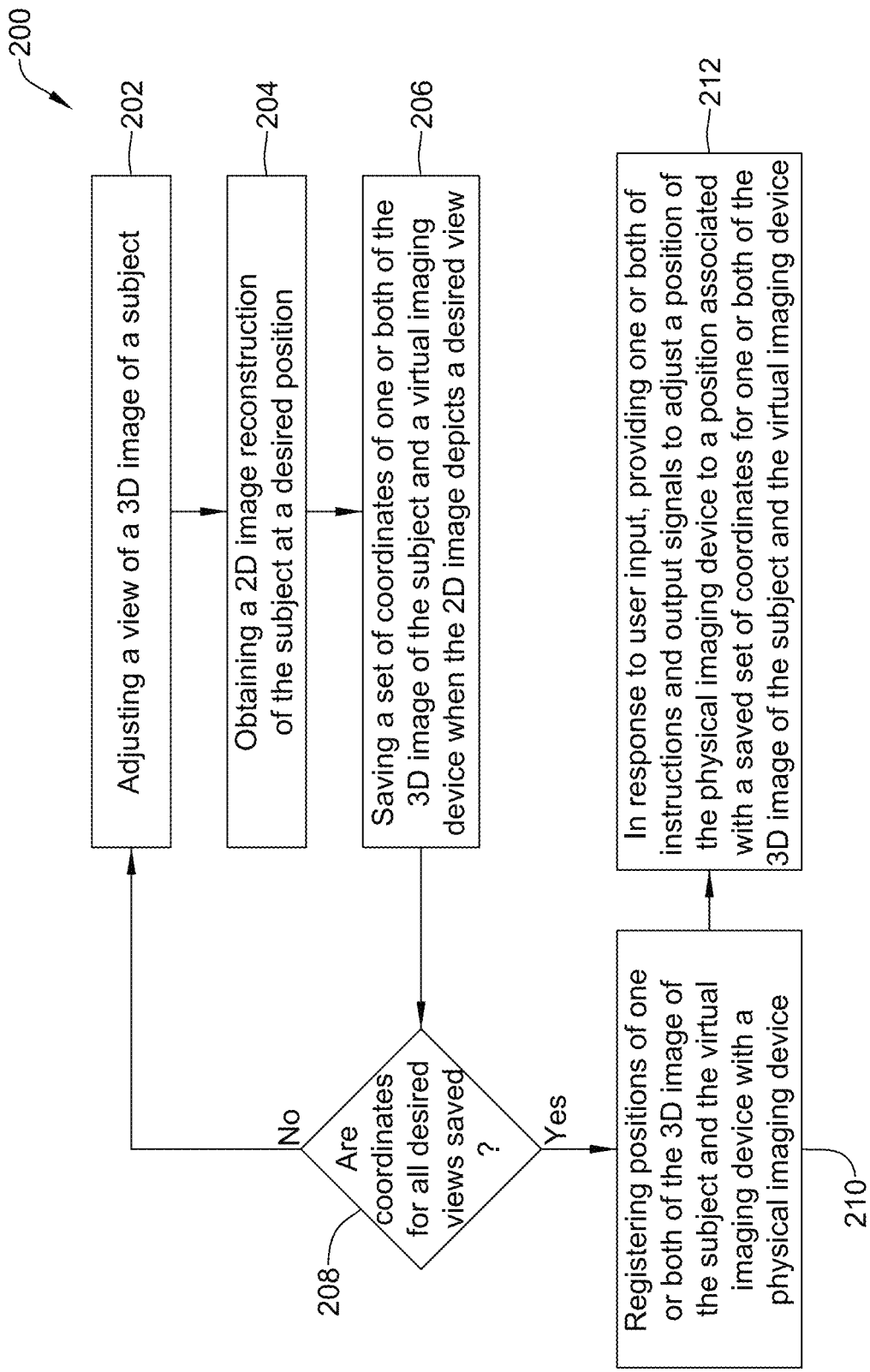
FIG. 5 is a schematic diagram of an illustrative method for use with an imaging system.

FIG. 5 depicts an illustrative method 200 for use with an imaging system (e.g., the imaging system 10 and/or other suitable imaging system). The method 200 may be configured to facilitate positioning a physical imaging device (e.g., the imaging device 14 and/or other suitable imaging device). Similar to as discussed elsewhere herein, the method 200 may include the use of a 3D image or data set having an adjustable view.

Similar to feature 102 of the method 100, the method 200 may include adjusting 202 a view of the 3D image of the subject (e.g., to a desired view or other suitable view), where a position address (e.g., coordinates and/or other suitable position address) of the 3D image or data set may be identified and associated with a depicted view of the 3D image or data set.

The adjusting of the view of the 3D image may occur in any suitable manner. In one example, adjusting the view of the 3D image of the subject may include adjusting a position of the 3D image of the subject relative to a virtual imaging device, adjusting a position of the virtual imaging device relative to the 3D image, and/or adjusting the 3D image and the virtual imaging device relative to the other. Further, a computing device (e.g., the computing device or controller 40 and/or other suitable computing device) may receive user input via a user interface (e.g., the user interface 50 and/or other suitable user interface) and in response to receiving the user input, the computing device may adjust the view of the of the 3D image or data set of the subject as instructed. In some cases, the computing device may adjust the view of the 3D image or data set of the subject in response to movement of the physical imaging device.

Once or as a view of the 3D image or data set of the subject is adjusted, a 2D image reconstruction (e.g., the synthetic or reconstructed 2D image 82 and/or other suitable reconstructed 2D image) may be obtained 204 from the 3D image or data set of the subject. The obtained 2D image reconstruction is intended to mimic or provide a prediction of a 2D image that could be obtained from the physical imaging device if the imaging device were imaging the 3D image or data set at the desired view. When the 3D image or data set of the subject is a CT scan, the 2D image reconstruction may be a DRR image and may be obtained using known techniques for producing digitally reconstructed radiograph images.

Similar to as discussed above with respect to feature 104 of the method 100, a user may view the 2D image reconstruction to determine if the 3D image is at a desired view useful for the procedure or other purposes. If 2D image reconstruction is not a useful view, the 3D image may be further adjusted until the 2D image reconstruction is believed to depict a useful view. Thus, a desired view of the 3D image may result in a 2D reconstruction view believed to be useful to a user during a procedure.

The method 200 may further include saving 206 a set of coordinates (e.g., a position address) of one or both of the 2D image of the subject and the virtual imaging device when the 2D image depicts a desired view. Although not required, the obtained 2D image reconstruction may be saved in memory along with the set(s) of coordinates of the 3D image or data set and/or the virtual imaging device. The sets of coordinates and/or the 2D image reconstructions may be saved in memory of any suitable computing device (e.g., the base unit 12, the imaging device 14, the control panel 24, the image processing device 26, a remote server, etc.) accessible by one or more components of the imaging system.

In some cases, features 202-206 may be performed prior to the 3D image or data set of the subject being registered to a physical imaging device in a procedure room. Such a configuration may utilize a pre-procedure 3D scan of the subject to identify a list of views of the subject prior to the procedure that will be useful during the procedure in order to save time during the procedure.

Once a set of coordinates has been saved, a determination 208 may be made as to whether coordinates for all desired views have been saved. If coordinates are not saved for all desired views (e.g., at least the desired views identifiable pre-procedure), the features 202, 204, and 206 may be repeated.

If coordinates are saved for all desired views, the method 200 may move to registering 210 positions of one or both of the 3D image or data set of the subject and the virtual imaging device (e.g., a coordinate system thereof) with positions of the physical imaging device relative to the subject in a procedure room (e.g., a coordinate system of the physical imaging device relative to the subject). Further, although the registering is depicted as occurring after the coordinates are saved, the registering may occur before, between, and/or during features 202, 204, and 206.

Registering of the 3D image of the subject and/or the virtual imaging device with the physical imaging device may done using any suitable registration or mapping technique. Although other techniques are contemplated, example techniques for registering or mapping a 3D image of a subject and/or the virtual imaging device to or with positioning of the physical imaging device 14 relative to a current position of a subject are described in PCT Application Publication No. WO2021061924A1 filed on Sep. 24, 2020 and titled SYSTEMS AND METHODS FOR UPDATING THREE-DIMENSIONAL MEDICAL IMAGES USING TWO-DIMENSIONAL INFORMATION, which is hereby incorporated by reference in its entirety for any and all purposes, and PCT Application Publication No. WO2021061960A1 filed on Sep. 24, 2020 and titled SYSTEMS AND METHODS FOR THREE-DIMENSIONAL NAVIGATION OF OBJECTS, which is hereby incorporated by reference in its entirety for any and all purposes. An example technique for registering or mapping a 3D image of a subject and/or the virtual imaging device to or with positioning of the physical imaging device 14 relative to a current position of a subject is described herein with respect to FIG. 7.

After registration or mapping of the 3D image of the subject and/or the virtual imaging device with the physical imaging device, one or both of instructions and output signals may be provided 212 in response to user input to adjust a position of the physical imaging device to a registered position associated with a saved set of coordinates for one or both of the 3D image of the subject and the virtual imaging device. In some cases, the instructions and/or output signals to adjust a position of the physical imaging device may be provided in response to user input (e.g., input into one or more user interface components discussed herein). Further, the provided instructions and/or provided output signal may be provided similar to as discussed above with respect to features 110 and 112 of the method 100.

The user input of feature 212 may be any suitable user input. In some cases, the user input of feature 212 may include the imaging system receiving a user selection of a 2D image reconstruction of the subject (e.g., a synthetic or reconstructed 2D image of the subject from the 3D image or data set) that is associated with a position address of the 3D image or data set of the subject in the pre-determined list of views of the subject. Then, based on the registration of the 3D image or data set with the physical imaging device and the selection of the 2D image reconstruction, a position for the physical imaging device that is associated with the position address of the three-dimensional image of the subject related to the selected 2D image reconstruction may be identified. Once the position for the physical imaging device has been identified, an image may be captured by the physical imaging device from the identified position.

Figure 6:
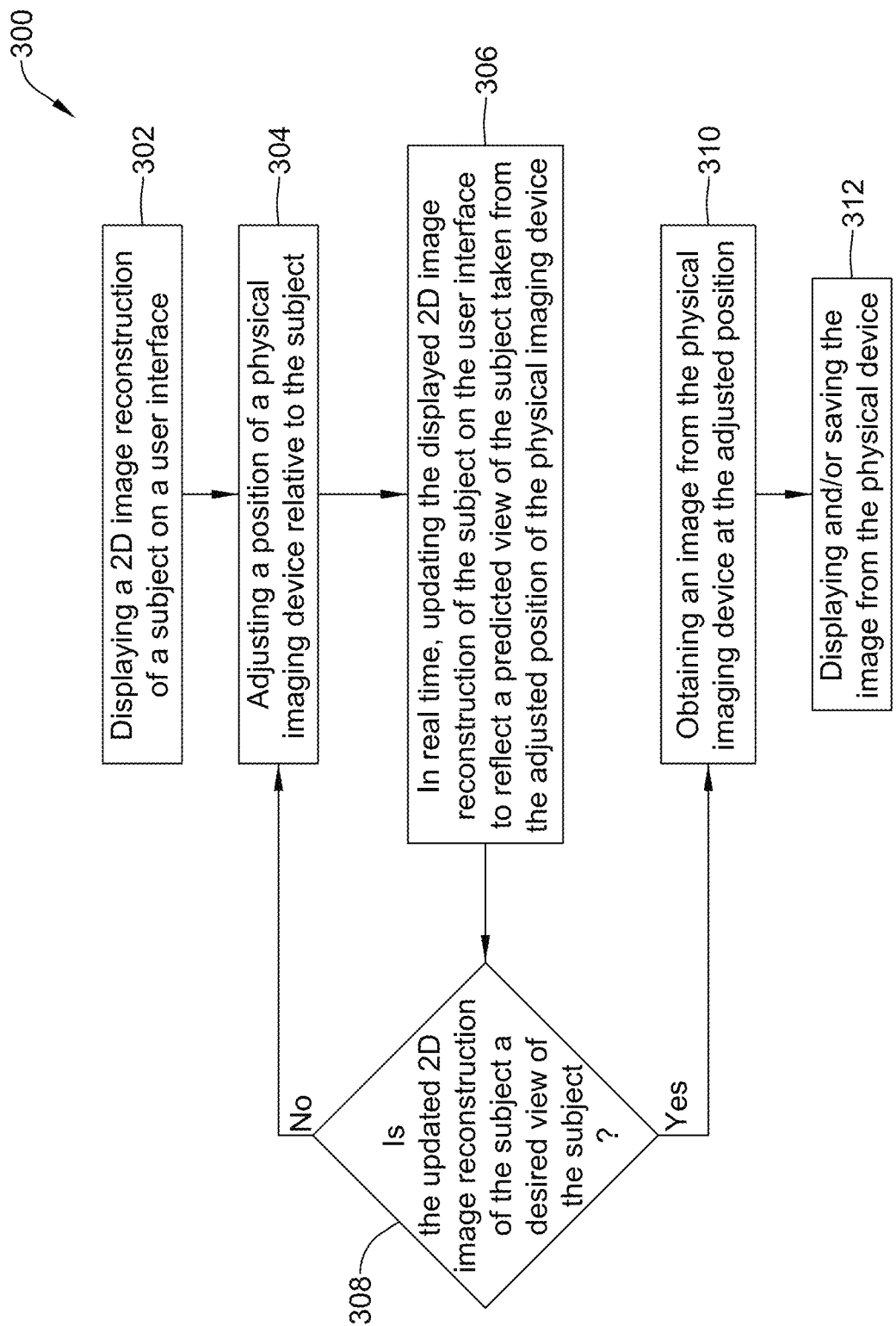
FIG. 6 is a schematic diagram of an illustrative method for use with an imaging system.

FIG. 6 depicts an illustrative method 300 for use with an imaging system (e.g., the imaging system 10 and/or other suitable imaging system). The method 300 may be configured to facilitate positioning a physical imaging device (e.g., the imaging device 14 and/or other suitable imaging device) in a procedure room, while mitigating radiation exposure in the procedure room. Moreover, the method 300 may facilitate a user understanding the view of the subject that would be in an image if the physical imaging device were to take or capture an image of the subject from its current position in a procedure room without actually capturing an image with the physical imaging device.

The method 300 may include displaying 302 a 2D image reconstruction of a subject on a user interface (e.g., the user interface 50 and/or other suitable user interface associated with a computing device). As discussed herein, the 2D image reconstruction of the subject may be obtained from a view of a 3D image or data set of the subject and may be considered to be a synthetic or reconstructed 2D image of a view of the 3D image or data set of the subject. In some cases, the 3D image or data set of the subject may be of an anatomy (e.g., a spine and/or other suitable anatomy) of the subject that is of interest for a procedure on the subject (e.g., a spinal surgical procedure and/or other suitable procedure).

The displayed 2D image reconstruction of the subject may be any suitable 2D image reconstruction of the subject. In one example of the displayed 2D image reconstruction, the displayed 2D image reconstruction of the subject may be representative of a 2D image captured by the physical imaging device in the procedure room at its current position. In another example of the displayed 2D image reconstruction, the displayed 2D image reconstruction of the subject may be a default initial view of the subject. Example initial views may include, but are not limited to, a lateral or oblique view, an A/P view, and/or other suitable views. In a further example of the displayed 2D image reconstruction, the displayed 2D image reconstruction of the subject may be a 2D image reconstruction of the subject at a view of the 3D image or data set of the subject. Other views in the displayed 2D image reconstructions of the subject are contemplated. Further, it is contemplated that a 2D image reconstruction may not be displayed until an initial adjustment of the physical imaging device.

The method 300 may further include adjusting 304 a position of the physical imaging device relative to the subject in the procedure room. In some cases, the physical imaging device may be adjusted to take or capture images of the subject from different perspectives to facilitate performing a procedure (e.g., a spinal surgical procedure and/or other suitable procedure) on the subject and/or other purposes.

Adjusting the position of the physical imaging device may be done in any suitable manner. For example, adjusting a position of the physical imaging device may be done manually and/or in response to received control signals. In some cases, instructions may be provided for directing a user how to manually adjust the physical imaging device. The instructions and/or control signals, when provided or received respectively, may be initiated in response to receiving user interactions with a user interface and/or may be automatically initiated based on a trigger event (e.g., a previous image capture, a startup of the physical imaging device, a surpassed threshold, etc.). In some cases, the physical imaging device may be adjusted to a predetermined position or location (e.g., a position or location (e.g., a position address) associated with a predetermined position address in a list of predetermined position addresses of the 3D image from which the 2D image reconstruction of the subject is produced, such as discussed herein and/or other suitable lists of predetermined position addresses).

The 2D image reconstruction of the subject on the user interface may be updated 306 to reflect a predicted view of the subject if an image were taken or captured from the adjusted position of the physical imaging device. Although not required, the displayed 2D image reconstruction of the subject on the user interface may be updated in real time as the physical imaging device is moved. Additionally or alternatively, the displayed 2D image reconstruction of the subject on the user interface may be updated in response to moving/adjusting the physical imaging device to a position or location and a user or system taking an action to set the position or location, which may cause an image processing system (e.g., the image processing device 26 and/or other suitable image processing system) to update the displayed 2D image reconstruction for the set position or location. In some cases, the displayed 2D image reconstruction of the subject on the user interface may be updated in real time as the physical imaging device is moved or adjusted and the updated 2D image reconstruction may be enhanced in response to a user or system setting a position or location of the physical imaging device.

In some cases, moving or adjusting the physical imaging device relative to the subject may cause a view of the 3D image or data set of the subject to adjust, which may cause the 2D image reconstruction of the subject to be updated. Alternatively or additionally, the physical imaging device may be adjusted to positions or locations (e.g., position addresses) associated with predetermined position addresses of the 3D image of the subject and the 2D image reconstruction of the subject for the predetermined position addresses of the 3D image of the subject, and when so adjusted, the updated 2D image reconstruction of the subject may be the 2D image reconstruction of the subject for the predetermined position address of the 3D image of the subject.

Registration or mapping of the 3D image or data set of the subject or an associated virtual imaging device with the physical imaging device relative to the subject in the procedure room may facilitate updating the displayed 2D image reconstruction of the subject on the user interface in response to adjusting a position of the physical imaging device. Registering of the 3D image or data set of the subject and/or the virtual imaging device with the physical imaging device may done using any suitable registration or mapping technique. Although other techniques are contemplated, an example registration or mapping technique is described herein with respect to FIG. 7.

After adjusting the position of the physical imaging device and updating the displayed 2D image reconstruction of the subject, a determination 308 may be made as to whether the updated 2D image reconstruction of the subject is a desired view of the subject. A desired view may be subjective to a user and may be based on one or more factors. Example factors for determining whether a view of the subject is a desired view are whether the view would be useful in furthering a future step of the procedure on the subject, whether the view depicts a result of a step of a procedure on the subject, etc. If the updated 2D image reconstruction of the subject is not a desired view, the method 300 may return to adjusting 304 the position of the physical imaging device relative to the subject. If the updated 2D image reconstruction of the subject is a desired view, an image from the physical imaging device may be taken, captured, or otherwise obtained 310 and displayed and/or saved 312.

In some cases, the imaging system may be configured such that the obtained image from the adjusted position of the physical imaging device may have a view of the subject that matches a view of the subject in the updated 2D image reconstruction. The obtained image may match the view of the subject in the 2D image reconstruction when the obtained image is the same as or is substantially the same as the view of the subject in the 2D image reconstruction. Similar to as discussed above with respect to the method 100, a computer vision algorithm may be utilized to compare the obtained image to the updated 2D image reconstruction. When the computer vision algorithm determines the obtained image does not match the 2D image reconstruction, an alert, instructions, and/or control signals may be determined and/or provided for indicating there is no match and the physical imaging device may need to be adjusted and/or re-registered with the 3D image of the subject. Alternatively or additionally, one or more users may visually compare, on one or more user interfaces, the image taken from the physical imaging device with the updated 2D image reconstruction of the subject.

Further, the registration or mapping between the 3D image or data set and the physical imaging device may be updated (e.g., automatically or in response to receiving a user interaction with a user interface), in real time or otherwise, in response to each image or set of images (when a burst of images is captured) that are captured or obtained with the physical imaging device. Such updating of the registration or mapping may assist in accounting for position changes of the physical imaging device relative to the subject over time and/or errors in the registration or mapping.

As discussed herein, a variety of techniques may be utilized for registering or mapping a 3D image of a subject to or with positioning of the imaging device 14 relative to a current position of a subject. Although other techniques are contemplated, FIG. 7 schematically depicts an illustrative technique for registering or mapping a 3D image of a subject to or with positioning of the imaging device 14 relative to a current position of the subject (e.g., mapping a coordinate system of the 3D image to a coordinate system of the imaging device 14).

Figure 7:
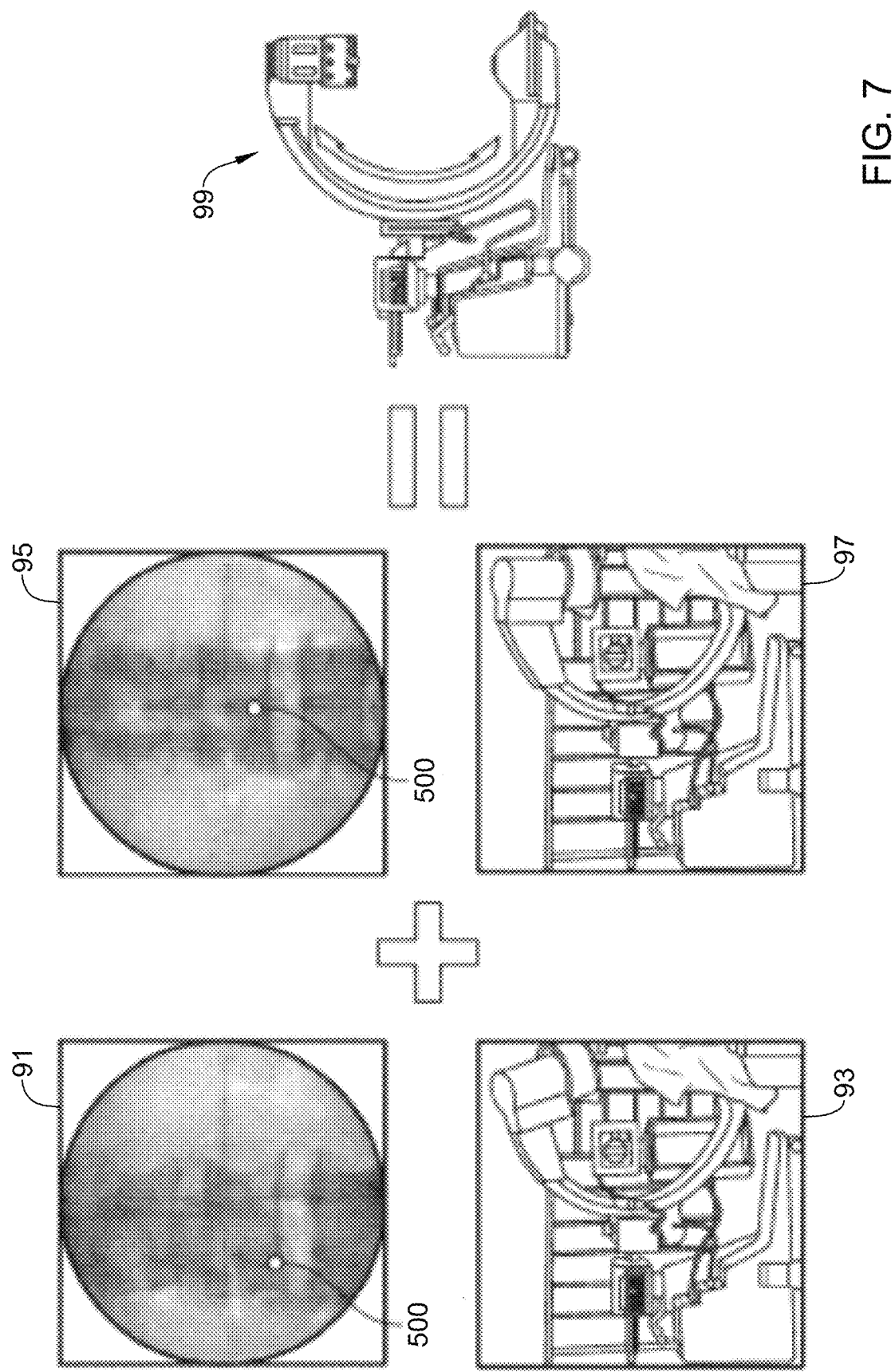
FIG. 7 is a schematic diagram of an illustrative image registration system.

Although other registering or mapping techniques are contemplated, the illustrative technique of FIG. 7 uses (e.g., via a computing device, controller, processor, etc.) images captured by the imaging device 14 and synthetic or reconstructed 2D images obtained from the 3D image of the subject to register or map the 3D image to the imaging device 14. In some cases, the registering or mapping of the 3D image of the subject to the imaging device 14 relative to a current position of the subject may be done in real time.

In one example implementation of registering or mapping a 3D image of a subject to the mapping device, a first 2D image 91 of the subject may be obtained from the imaging device when the imaging device is at a first location (e.g., a first location having a first set of coordinates) and a second 2D image 95 of the subject may be obtained from the imaging device when the imaging device is at a second location (e.g., and a second location having a second set of coordinates). In some cases, one of the first 2D image and the second 2D image may be an oblique or lateral image (e.g., the first 2D image 91 in FIG. 7) of the subject taken with the imaging device 14 and the other of the first 2D image and the second 2D image may be an A/P image (e.g., the second 2D image 95 in FIG. 7) of the subject taken with the imaging device 14. It is contemplated that one or more additional and/or alternative suitable images of the subject taken with the imaging device 14 at known locations of the imaging device 14 may be utilized for registering or mapping the 3D image of the subject with the imaging device 14. Further, the images taken with the imaging device 14 may include a reference marker 500, where the reference marker 500 in the images is a feature in or on the subject at the time of taking the images and is of known dimensions, geometry, and/or angular position information (e.g., from the imaging device 14 and/or surgical instruments), but use of a reference marker is not required.

In the example implementation of registering or mapping, a processing unit (e.g., of the computing device or controller 40 and/or of other suitable computing devices) may compare the first image 91 obtained from the imaging device 14, information regarding a location or position of the imaging device 14 when taking the first image 91 as represented by the box 93, the second image 95 obtained from the imaging device 14, and information regarding a location position of the imaging device 14 when taking the second image 95 as represented by the box 97 with one or more synthetic or reconstructed 2D images from one or more desired views of the 3D image to determine or calculate an alignment of the 3D image positioning (e.g., a coordinate system of the 3D image) with the positioning of the imaging device 14 (e.g., a coordinate system of the imaging device 14) relative to the subject. In some cases, the determining or calculating of an alignment 99 of the 3D image position with the positioning of the imaging device 14 relative to the current position of the subject may include associating position addresses of the 3D image with positions of the imaging device 14 based on a location (e.g., a first location) of the imaging device 14 when capturing the first image 91, a location (e.g., a second location) of the imaging device 14 when capturing the second image 95, and a comparison of the first image 91 and the second image 95 to a synthetic or reconstructed 2D image from the 3D image of the subject.

In addition to or as an alternative to the techniques described with respect to FIG. 7, the system may register the 3D image with the imaging device, and/or adjust the registration, in response to a user's manual adjustments. In one example, after the user views a captured 2D image adjacent a reconstructed or synthetic 2D preview image, the user may adjust (e.g., via user interface controls and/or other suitable controls) the reconstructed or synthetic 2D preview image to exactly match, or as nearly as possible match, the captured 2D image. Such manual adjustment of the reconstructed or synthetic 2D preview image may be facilitated by overlaying the reconstructed or synthetic 2D image on the captured image and adjusting the 3D image and/or the physical imaging device until the reconstructed or synthetic 2D image matches the captured image, but this is not required.

The manual adjustment of the reconstructed or synthetic 2D preview image may be independent of or supplemented with automated adjustment of the reconstructed or synthetic 2D preview image. In response to the adjustment of the reconstructed or synthetic 2D preview image to match the captured image, the image processing device may update the registration of the 3D image with the imaging device based on the adjustment of the reconstructed or synthetic 2D preview image and a position (e.g., coordinates) of physical imaging device at the time of capturing the captured 2D image.

Based on the registration of the 3D image with the imaging device 14, a user is able to determine position information (e.g., a set of coordinates) for the imaging device 14 that is associated with a synthetic or reconstructed 2D image depicting a desired view of a subject based on coordinates of the 3D image associated with the synthetic or reconstructed 2D image depicting the desired view. Similarly, once registration is complete, synthetic or reconstructed 2D images from the 3D image of the subject may be displayed in real time in response to movement of the imaging device 14.

Unless expressly indicated otherwise, the systems, devices, techniques, and methods described herein may be used together, in a complementary manner, and/or features of the techniques and methods may be repeated, as desired. Additionally or alternatively, the techniques and methods described herein may be effected entirely or at least partially by one or more computing devices (e.g., the computing device or controller 40 and/or other suitable computing devices or controllers), where the techniques and/or methods may be stored, in a non-transitory state, as instructions and/or program code in memory (e.g., a computer readable medium) of the computing devices and a processor of the computing devices may be configured to execute the stored instructions and/or program code.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

This detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A method for use with an imaging system having an imaging modality from at least one of an X-ray, a computerized tomography (CT), a magnetic resonance imaging (MRI), an ultrasound, a positron emission tomography (PET), a single-photon emission computed tomography (SPECT), an optical coherence tomography (OCT), a fluorescence imaging, a fluoroscopic imaging, and an infrared imaging, the method comprising:
    adjusting a view of a three-dimensional image of a subject to a desired view of the three-dimensional image;
    obtaining a two-dimensional image reconstruction from the three-dimensional image of the subject at the desired view;
    identifying a physical position for a physical imaging device that is associated with the desired view,
    adjusting the view of the three-dimensional image of the subject to a plurality of desired views;
    obtaining two-dimensional images from the three-dimensional image of the subject at each of the plurality of desired views;
    identifying a position address of the three-dimensional image of the subject at each of the plurality of desired views; and
    storing the identified position addresses of the three-dimensional image of the subject.

2. The method of claim 1, further comprising:
    providing instructions, in real time, for moving the physical imaging device to the physical position for the physical imaging device that is associated with the desired view.

3. The method of claim 1, further comprising:
    providing control signals to adjust a location of the physical imaging device to the physical position for the physical imaging device that is associated with the desired view.

4. The method of claim 1, wherein adjusting the view of the three-dimensional image of the subject to the desired view of the three-dimensional image includes adjusting a position of one or both of the three-dimensional image of the subject and a virtual imaging device to a desired position relative to the other of the three-dimensional image of the subject and the virtual imaging device.

5. The method of claim 1, further comprising:
    identifying a position address for the three-dimensional image of the subject at the desired view; and
    wherein the position for the physical imaging device associated with the desired view is based on the position address.

6. The method of claim 1, further comprising:
    identifying positions for the physical imaging device that are associated with each of the plurality of desired views.

7. The method of claim 1, wherein the adjusting the view of the three-dimensional image of the subject to the desired view is in response to adjusting a position of the physical imaging device.

8. The method of claim 1, further comprising:
    registering position addresses of the three-dimensional image with positions of the physical imaging device.

9. The method of claim 8, wherein registering position addresses of the three-dimensional image with positions of the physical imaging device comprises:
    obtaining a first image of the subject from the physical imaging device at a first location of the physical imaging device;
    obtaining a second image of the subject from the physical imaging device at a second location of the physical imaging device;
    comparing the first image of the subject and the second image of the subject to the two-dimensional image reconstruction from the three-dimensional image of the subject; and
    associating the position addresses of the three-dimensional image with the positions of the physical imaging device based on the first location, the second location, and the comparison of the first image of the subject and the second image of the subject to the two-dimensional image reconstruction from the three-dimensional image of the subject.

10. The method of claim 1, wherein the physical imaging device is a two-dimensional imaging device and the three-dimensional image is obtained from a three-dimensional physical imaging device.

11. The method of claim 1, further comprising:
    obtaining a two-dimensional image with the physical imaging device positioned at or proximate to the position; and
    providing the two-dimensional image for use by a surgeon during a spinal fusion procedure.

12. A system comprising:
    a user interface including a display;
    an imaging device having an imaging modality from at least one of an X-ray, a computerized tomography (CT), a magnetic resonance imaging (MRI), an ultrasound, a positron emission tomography (PET), a single-photon emission computed tomography (SPECT), an optical coherence tomography (OCT), a fluorescence imaging, a fluoroscopic imaging, and an infrared imaging; and
    a controller coupled to the imaging device and the user interface, the controller is configured to store data related to one or more images of a subject and is programmed to:
    adjust a view of a three-dimensional image of a subject on the display to a desired view having an associated three-dimensional address;
    create a synthetic image from the three-dimensional image of the subject at the desired view;
    obtain a captured image from the imaging device, wherein the captured image is configured to have a view of the subject that matches a view of the subject in the synthetic image,
    adjusting the view of the three-dimensional image of the subject to a plurality of desired views;
    obtaining two-dimensional images from the three-dimensional image of the subject at each of the plurality of desired views;
    identifying a position address of the three-dimensional image of the subject at each of the plurality of desired views; and
    storing the identified position addresses of the three-dimensional image of the subject.

13. The system of claim 12, wherein the controller is further programmed to:
  associate a position for the imaging device with the three-dimensional address, the associated position for the imaging device is configured to result in the captured image having the view of the subject that matches the view of the subject in the synthetic image.

14. The system of claim 12, wherein the adjusting the view of the three-dimensional image of the subject on the display to the desired view is in response to adjusting a position of the imaging device.

15. The system of claim 12, wherein the adjusting the view of the three-dimensional image of the subject to the desired view is in response to receiving user interaction over the user interface.

16. The system of claim 12, wherein the controller is further programmed to provide at least one output selected from the following outputs:
  instructions, in real time, for moving the imaging device to a position for taking the captured image that results in the captured image having the view of the subject that matches the view of the subject in the synthetic image; and
  control signals to move the imaging device to the position for taking the captured image that results in the captured image having the view of the subject that matches the view of the subject in the synthetic image.

17. A computer readable medium having stored thereon in a non-transitory state a program code for use by a computing device, the program code causing the computing device to execute a method to assist in capturing images during surgery on a subject, the images from an imaging modality from at least one of an X-ray, a computerized tomography (CT), a magnetic resonance imaging (MRI), an ultrasound, a positron emission tomography (PET), a single-photon emission computed tomography (SPECT), an optical coherence tomography (OCT), a fluorescence imaging, a fluoroscopic imaging, and an infrared imaging, the method comprising:
  selecting a synthetic image of a subject from one or more stored synthetic images of the subject, the synthetic image is associated with an address of a three-dimensional image of the subject;
  identifying a position for an imaging device that is associated with the address of the three-dimensional image of the subject;
  causing the imaging device to capture an image from the position for the imaging device that is associated with the address of the three-dimensional image of the subject; and
  adjusting a position of the three-dimensional image of a subject to the address of the three-dimensional image in response to one or both of movement of the imaging device and user interactions with a user interface.

18. The computer readable medium of claim 17, wherein the method further comprises
  providing at least one of:
    instructions, in real time, for moving the imaging device to the position for the imaging device that is associated with the address of the three-dimensional image of the subject; and
    control signals to move the imaging device to the position for the imaging device that is associated with the address of the three-dimensional image of the subject.

* * * * *